United States Patent [19]

Ison

[11] 4,172,203
[45] Oct. 23, 1979

[54] METHOD FOR PREPARING DICHLOROMETHYL PYRIDINES

[75] Inventor: Robin R. Ison, Concord, Calif.

[73] Assignee: The Dow Chemical Company, Midland, Mich.

[21] Appl. No.: 933,316

[22] Filed: Aug. 14, 1978

[51] Int. Cl.$^2$ .......................................... C07D 213/26
[52] U.S. Cl. ................................... 546/345; 546/346
[58] Field of Search ............... 260/290 HL; 546/345, 546/346

[56] References Cited

U.S. PATENT DOCUMENTS

| | | | |
|---|---|---|---|
| 3,234,229 | 2/1966 | Redemann | 260/295 R |
| 3,971,799 | 7/1976 | McGregor | 260/295 R |

*Primary Examiner*—Alan L. Rotman
*Attorney, Agent, or Firm*—Gary D. Street

[57] ABSTRACT

Dichloromethylpyridine derivatives are prepared from hydrazino adducts of trichloromethylpyridine compounds by reacting said adducts with an aqueous alkaline solution in the presence of a refluxing carrier medium.

9 Claims, No Drawings

METHOD FOR PREPARING DICHLOROMETHYL PYRIDINES

BACKGROUND OF THE INVENTION

Hydrazino adducts of chloro-substituted trichloromethyl pyridine compounds, such as 2,3,5-trichloro-4-hydrazino-6-(trichloromethyl)pyridine and similar mono-or di-chloro ring-substituted compounds are known and can be prepared according to known procedures. See, for example, U.S. Pat. No. 3,234,229. Dechlorination of a ring chlorine substituent from chloro-substituted picolinic acid compounds by treating a hydrazino adduct thereof with a base and sodium hypochlorite solution is also known in the art. See U.S. Pat. No. 3,971,799. Similarly, the ring dechlorination of chloro-substituted (trichloromethyl)pyridine compounds, such as 2,3,4,5-tetrachloro-6-(trichloromethyl)-pyridine, to a 2,3,5-trichloro-6-(trichloromethyl)pyridine compound, is carried out by forming the hydrazino adduct of the tetrachloro compound and then dehydrizinating the same with a sodium hypohalite solution in the presence of a carrier medium is also known to the applicant. Applicant and another also believed that treatment of such a hydrazino adduct with a mild aqueous base in the presence of a carrier medium resulted in the removal of an additional ring chlorine substituent along with the chlorine substituent replaced by the hydrazino adduct, yielding a 2,5-dichloro-6-(trichloromethyl)pyridine compound instead of the 2,3,5-trichloro-6-(trichloromethyl)pyridine compound. However, applicant has discovered that treatment of hydrazino adducts of trichloromethylpyridine compounds with a mild base in the presence of an inert carrier medium results in the side-chain dechlorination of the trichloromethyl group, rather than the expected ring dechlorination.

SUMMARY OF THE INVENTION

According to the present invention, dichloromethylpyridine compounds are obtained by a method which comprises treating hydrazino adducts of trichloromethyl substituted pyridine compounds with a weak alkaline base in the presence of an inert carrier medium. The hydrazino adducts of the trichloromethylpyridine compounds to be treated can optionally bear one or more ring chloro substituents in addition to the ring hydrazino substituent, thus giving chloro-substituted dichloromethylpyridine compounds. The substituted or unsubstituted dichloromethyl pyridine compounds prepared by the present invention have utility as herbicides and are also useful as intermediates in the preparation of other pesticidal compounds or other intermediates.

DETAILED DESCRIPTION OF THE INVENTION

The dichloromethylpyridine compounds which can be prepared according to the present invention include unsubstituted dichloromethylpyridine and chloro-substituted dichloromethylpyridine compounds bearing from 1 to 3 ring chloro substituents:

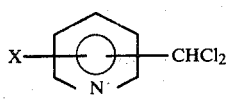

wherein X is 0 to 3, inclusive. Preferred compounds include those wherein the dichloromethyl group is in the 2-ring position. Preferred starting materials thus include those having a trichloromethyl group in the 2-ring position and a hydrazino group in the 4-ring position. The preferred starting materials can optionally bear 1–3 ring chlorine groups. A preferred compound prepared according to the present invention is 2-(dichloromethyl)-pyridine. In another preferred embodiment, chloro-substituted-2-(dichloromethyl)pyridine compounds are prepared according to the invention. Preferred chloro-substituted compounds include 3,5,6-trichloro-2-(dichloromethyl)pyridine, 2-chloro-6-(dichloromethyl)pyridine and 3,5-dichloro-2-(dichloromethyl)pyridine.

The hydrazino adducts of the (trichloromethyl)pyridine starting materials necessary to prepare the desired (dichloromethyl)pyridine compounds will be readily apparent to those of ordinary skill in the art and can be prepared from chloro-substituted (trichloromethyl) pyridine compounds according to known procedures. Typically, the chloro-substituted (trichloromethyl)pyridine reactant is reacted with equimolar or excess molar amounts of hydrazine and triethylamine in the presence of a solvent carrier, such as alcohols, toluene and the like. The reaction is usually carried out by heating the reaction mixture under reflux conditions and under a nitrogen atmosphere for a period of time sufficient to form the hydrazino adduct, usually from about 1 to about 6 hours. The hydrazino adduct can be recovered by mixing the reaction mixture with hot water to precipitate the desired hydrazino adduct.

In carrying out the method of the present invention, the hydrazino adduct of the (trichloromethyl)pyridine starting material is heated, preferably under reflux conditions, in a mixture with a weak-base and an inert carrier media. The reaction is usually carried out over a period of from about 1 to about 6 hours to substantially complete the dehydrazination of the hydrazino substituent and the dechlorination of a chlorine atom from the trichloromethyl substituent. The reaction mixture is then cooled, mixed with water and acidified with concentrated HCl, and the end product extracted into dichloromethane and dried over MgSO$_4$.

The relatively weak base which can be employed in the present invention is one which is effective to promote the dehydrazination and side-chain dechlorination of the starting material. Those which are not so operable are, of course, not within the scope of the present invention. Hypohalites, such as sodium hypochlorite, are not effective in promoting the dechlorination of the trichloromethyl side chain and are thus not within the scope of the present invention. Typical bases such as sodium hydroxide, potassium hydroxide, sodium carbonate and the like are effective bases which can be used in the present invention. Generally, the base is used in a slight molar excess over the starting material, a 1.1–1.5 or more molar excess usually being employed. Use of higher molar excesses, such as about 2 or more, are not desired as other problems may result. Usually, in carrying out the process of the present invention, the starting hydrazino(trichloromethyl)pyridine reactant is suspended in the carrier medium and the base added portionwise thereto with stirring. A preferred base for use in the invention is NaOH.

The inert carrier media which can be employed in the present invention include alcohols, such as methanol, ethanol, isopropyl alcohol, butanol, acetonitrile and the like, including mixtures thereof.

The following examples illustrate the invention but are not to be construed as limiting the same.

EXAMPLE 1

3,5-Dichloro-4-hydrazino-2-(trichloromethyl)pyridine (2.95 grams. 0.01 mole) was mixed with absolute methanol (50 ml) and an aqueous sodium hydroxide solution (1 N, 12.5 ml, 0.0125 mole) added thereto portionwise. The resulting mixture was heated under reflux for a period of about one and one-half hours and then cooled. The tarry mixture was mixed with water (100 ml), acidified with concentrated HCl, then extracted with dichloromethane. The product extract was dried over $MgSO_4$ and isolated by evaporation under reduced pressure. The structure of the product was confirmed by examination of gas liquid chromatography (GLC), mass spectral analysis and proton magentic resonance spectroscopy (PMR) to be the desired 3,5-dichloro-2-(dichloromethyl)pyridine compound, and not the 3- or 5-monochloro-2-(trichloromethyl)pyridine. The quantitative GLC assays (using an internal standard—1,2,3,4-tetrachlorobenzene) were conducted using a 6 ft.×2 mm I.D. glass column packed with 10% SP-2100 on 100/120 Supelcoport (Supelco, Inc.) with a Hewlett-Packard 5710 A gas chromatograph equipped with a thermal conductivity detector and interfaced with a Hewlett-Packard 3352 computerized integration system. The following operating conditions were used:

Oven temperature program, 150°–200° C. at 4°/min. with 2 min. hold at 200° C.

Injection Port, 200° C. Detector, 250° C.

Helium carrier gas flow rate, 30 ml/min.

One minute integration delay to avoid data collection of solvent peak.

Confirmatory proof of the structure was also obtained by distilling the crude product under vacuum. A small quantity was distilled over at 197°–202° C./105 mm/Hg and the colorless liquid solidified upon standing at room temperature. The melting point (60–62%) was in good agreement with an authentic sample of the named product (68°–69° C.). A mixed melting point of 61°–65° C. was recorded. The PMR spectrum of the product was identical to that of the named product.

EXAMPLE 2

The procedures of Example 1 were repeated to quantitate the yield of product. In the first run, the reaction mixture of the hydrazino compound (4.0 grams, 0.0135 mole), sodium hydroxide (1/N, 14.9 ml, 0.0149 ml and methanol (60/ml were heated under reflux for 2 hours while in the second run a reaction mixture of hydrazino compound (3.75 grams, 0.0127 mole), sodium hydroxide (1/N, 15 ml, 0.015 mole) and acetonitrile (100 ml) were heated under reflux conditions for a period of 3 hours. GLC assays indicated a 49% yield of desired product in the first run and a 64% yield of desired product in the second run.

EXAMPLE 3

In procedures as noted in Example 1, a reaction mixture of 4-hydrazino-2,3,5-trichloro-6-(trichloromethyl)-pyridine (9.9 grams; 0.03 mole) and sodium hydroxide (1/N, 37.5 ml, 0.0375 mole) in methanol (100 ml) was heated under reflux conditions for a period of about 4 hours and the product similarly recovered as a brown oil. Examination of GLC, PMR and mass spectral analysis indicated a product yield of 59% of 3,5,6-trichloro-2-(dichloromethyl)pyridine. A portion of the crude product was distilled over at 168°–73° C./21 mmHg as a colorless oil which crystallized as large colorless prisms from hexane, m.p. 61°–62° C.

Calculated for $C_6H_2Cl_5N$: C, 27.15; H, 0.76; N, 5.28%. Found: C, 27.20; H, 0.87; N, 5.13%.

EXAMPLE 4

In other runs using the procedure of Example 1 above, the reactants of Example 3 above were run in the presence of different carrier media and reaction periods and the product yield of the 3,5,6-trichloro-2-(dichloromethyl)pyridine compound determined as follows:

TABLE I

| Run No. | Carrier Media | Reaction Time/Hrs. | Product Yield% |
|---|---|---|---|
| 1 | Methanol | 4 | 59 |
| 2 | " | 2 | 75 |
| 3 | Ethanol | 2.75 | 69 |
| 4 | Isopropanol | 2.25 | 71 |
| 5 | Acetonitrile | 2.75 | 83 |

EXAMPLE 5

A mixture of 3,4,5-trichloro-2-trichloromethylpyridine (92.4%, 12.98 g, 0.04 mole), hydrazine hydrate (85.5%, 2.93 g, 0.05 mole) and triethylamine (5.05 g, 0.05 mole) in methanol (100 ml) was heated under reflux in an atmosphere of nitrogen for 4 hours. The hot solution was poured into water (150 ml) whereupon the product precipitated out. After the mixture had cooled to room temperature, the 3,5-dichloro-4-hydrazino-2-(trichloromethyl)pyridine product was filtered off, washed with water, and dried.

Yield: 11.76 g (99%), m.p. 175°–78° C.

Recrystallization from acetonitrile gave an analytical sample, m.p. 174°–7° C.

Calculated for $C_6H_4Cl_5N_3$: C, 24.39, H, 1.36; N, 14.23%. Found: C, 24.56; H, 1.50; N, 13.98%.

EXAMPLE 6

A mixture of 3,4,5,6-tetrachloro-2-(trichloromethyl)-pyridine (6.68 grams, 0.02 mole) hydrazine hydrate (85.5%, 1.47 g, 0.025 mole), triethylamine (3.03 g, 0.03 mole) and butylated hydroxytoluene (0.22 g, 0.001 mole) in methanol (50 ml) was heated under reflux in an atmosphere of nitrogen for 2.25 hours. The hot solution was poured into water and the precipitated product filtered off and dried. The desired starting material, 4-hydrazino-2,3,5-trichloro-6-trichloromethylpyridine, having an m.p. 107°–9° C. was thus obtained. Yield, based on starting material, was 98%.

Other dichloromethylpyridine compounds are similarly prepared according to the method of the present invention. The best mode for carrying out the process of the invention with a chloro-substituted 4-hydrazino-2-(trichloromethyl)pyridine reactant and treating the same with a slight molar excess of 1.0 N NaOH in the presence of acetonitrile, the reaction mixture being heated at reflux for about 2½–3 hours.

What is claimed is:

1. A method of preparing dichloromethylpyridine compounds which comprises heating a hydrazino adduct of a trichloromethylpyridine compound with a weak base effective to promote dehydrizination and side-chain dechlorination thereof, said method being carried out in the presence of an inert carrier medium, and thereafter recovering said dichloromethyl pyridine compound.

2. The method of claim 1 wherein said heating is carried out under reflux conditions.

3. The method of claim 1 wherein dichloromethyl pyridine compound is prepared.

4. The method of claim 1 wherein a chloro-substituted dichloromethyl pyridine compound is prepared.

5. The method of claim 3 wherein said heating is carried out under reflux conditions.

6. The method of claim 5 wherein 6-(dichloromethyl)pyridine is prepared.

7. The method of claim 4 wherein said heating is carried out under reflux conditions.

8. The method of claim 7 wherein 3,5-dichloro-2-(dichloromethyl)pyridine is prepared.

9. The method of claim 7 wherein 3,5,6-trichloro-2-(dichloromethyl)pyridine is prepared.

* * * * *